(12) United States Patent
Xia et al.

(10) Patent No.: US 11,767,506 B2
(45) Date of Patent: Sep. 26, 2023

(54) IN VITRO MATURATION CULTURE MEDIUM OF IMMATURE OOCYTES AND USE THEREOF

(71) Applicant: CHINA AGRICULTURAL UNIVERSITY, Beijing (CN)

(72) Inventors: Guoliang Xia, Beijing (CN); Chao Wang, Beijing (CN); Huarong Wang, Beijing (CN); Han Cai, Beijing (CN)

(73) Assignee: CHINA AGRICULTURAL UNIVERSITY, Beijing (CN)

( * ) Notice: Subject to any disclaimer, the term of this patent is extended or adjusted under 35 U.S.C. 154(b) by 602 days.

(21) Appl. No.: 16/650,168

(22) PCT Filed: Oct. 13, 2017

(86) PCT No.: PCT/CN2017/106067
§ 371 (c)(1),
(2) Date: Mar. 24, 2020

(87) PCT Pub. No.: WO2019/061560
PCT Pub. Date: Apr. 4, 2019

(65) Prior Publication Data
US 2020/0224158 A1      Jul. 16, 2020

(30) Foreign Application Priority Data
Sep. 30, 2017   (CN) .......................... 201710920296.2

(51) Int. Cl.
*C12N 5/075*     (2010.01)
*C12N 5/00*      (2006.01)

(52) U.S. Cl.
CPC ......... *C12N 5/0609* (2013.01); *C12N 5/0018* (2013.01); *C12N 2500/32* (2013.01); *C12N 2501/30* (2013.01); *C12N 2501/73* (2013.01); *C12N 2502/243* (2013.01); *C12N 2517/10* (2013.01)

(58) Field of Classification Search
None
See application file for complete search history.

(56) References Cited

U.S. PATENT DOCUMENTS

| 2016/0032243 A1 | 2/2016 | Tian et al. |
| 2017/0342379 A1 | 11/2017 | Romero et al. |

FOREIGN PATENT DOCUMENTS

| CN | 102899286 | 1/2013 |
| CN | 103468639 | 12/2013 |
| CN | 104342400 | 2/2015 |
| CN | 107208057 | 9/2017 |
| WO | WO 2014/043835 | 3/2014 |
| WO | WO 2014/046983 | 3/2014 |
| WO | WO-2016094970 A1 * | 6/2016 | .............. A61P 15/00 |

OTHER PUBLICATIONS

Trounson, A., et al. "Oocyte maturation." Human Reproduction 13.suppl_3 (1998): 52-62. (Year: 1998).*
Coticchio et al. "Oocyte maturation: gamete-somatic cells interactions, meiotic resumption, cytoskeletal dynamics and cytoplasmic reorganization." Human reproduction update 21.4 (2015): 427-454. (Year: 2015).*
Davie, James R. "Inhibition of histone deacetylase activity by butyrate." The Journal of Nutrition 133.7 (2003): 2485S-2493S. (Year: 2003).*
Arora, Meenakshi. "Cell culture media: a review." Mater Methods 3.175 (2013): 24. (Year: 2013).*
Zwergel et al. "Emerging approaches for histone deacetylase inhibitor drug discovery." Expert Opinion on Drug Discovery 10.6 (2015): 599-613. (Year: 2015).*
Gutierrez et al. "Development of a long-term bovine granulosa cell culture system: induction and maintenance of estradiol production, response to follicle-stimulating hormone, and morphological characteristics." Biology of reproduction 56.3 (1997): 608-616. (Year: 1997).*
English translation of Office Communication issued in Japanese Patent Application No. 2020-517106, dated Apr. 21, 2021.
Extended European Search Report issued in European Patent Application No. 17926780.2, dated May 25, 2021.
Gao et al., "The effect of valproic acid on bovine oocyte maturation and early embryonic development in vitro," Cytotechnology, 66(3):525-532, 2014.
Liu et al., "Transient exposure to sodium butyrate after germinal vesicle breakdown improves meiosis but not developmental competence in pig oocytes," Cell Biology International, 36(5):483-490, 2012.
Lu et al., Effect of SAHA on Development Potency of Oocytes and Embryos of Buffalo (*Bubalus bubalus*)), Journal of Agricultural Biotechnology, 24(9):1450-1456, 2016. (English abstract of Chinese publication).
Marks and Jiang, "Histone Deacetylase Inhibitors in Programmed Cell Death and Cancer Therapy," Cell Cycle, 4(4):549-551, 2005.
PCT International Search Report issued in International Application No. PCT/CN2017/106067, dated Jul. 8, 2018.

* cited by examiner

Primary Examiner — Emily A Cordas
(74) Attorney, Agent, or Firm — Parker Highlander PLLC

(57) ABSTRACT

Provided is a method for culturing immature oocytes. The method can promote in vitro maturation of the immature oocytes, and specifically comprises using follicular cells and a culture medium for culturing same. The culture medium for culturing the follicular cells contains CNP or variants thereof or analogues thereof and an HDAC (histone deacetylase) inhibitor. Also provided are the in vitro maturation culture medium containing CNP or variants thereof or analogues thereof and the HDAC inhibitor, and related compositions thereof, and the use of the above medium, culture medium and compositions in the promotion of in vitro maturation of the immature oocytes.

12 Claims, 2 Drawing Sheets

IN VITRO MATURATION CULTURE MEDIUM OF IMMATURE OOCYTES AND USE THEREOF

CROSS REFERENCE TO RELATED APPLICATIONS

This application is a national phase application under 35 U.S.C. § 371 of International Application No. PCT/CN2017/106067, filed Oct. 13, 2017, which claims the priority of Chinese Patent Application No. 201710920296.2, filed on Sep. 30, 2017 and titled with "IN VITRO MATURATION CULTURE MEDIUM OF IMMATURE OOCYTES AND USE THEREOF," and the disclosures of each of which are hereby incorporated by reference.

FIELD

The present disclosure relates to a culture medium for promoting in vitro maturation of immature oocytes, related compositions, and a culture method, belonging to the field of medical biology.

BACKGROUND

In clinic practice for assisting human reproduction, gonadotropins are widely used to facilitate superovulation on female patients, and thereafter the obtained mature oocytes are subjected to in vitro fertilization or single sperm injection, and the like, to achieve the goal of breeding offspring. However, due to reasons such as environment, mental pressure and difference response to gonadotropin in individuals, after the superovulation operation, conditions that a certain number of the obtained oocytes are immature occur in some patients, which greatly reduce the success rate of performing assisted reproduction on the patient and decrease the utilization of the collected oocytes. It is a pity that the current method for promoting maturation of oocytes and the culture media used thereof in clinical practice cannot solve the above problem in certain extent. Thus, if a new method for in vitro culture of human immature oocytes is developed to promote the maturation and obtaining corresponding development potential of the immature oocytes after culturing them in vitro for a period of time, which will promote the improvement of assisted reproductive technology, increase the success rate of assisted reproduction and brings good news to the patients.

Nowadays, an important factor that limits the development of livestock reproduction industry in China is that, the number of high quality breeding stock is small and the speed of breeding is slow, resulting in a situation in which production performance is backward. The development of embryo engineering technology has greatly promoted the advancement of reproductive technology. To this end, it has become a technology platform and direction to transplant the embryos obtained by in vitro fertilization using embryo engineering technology to promote the development of animal husbandry. A common method is to obtain immature oocytes from the ovaries without hormone stimulated, and culture them until mature in an in vitro culture system for embryo production and animal reproduction. Unfortunately, currently, the number of in vitro produced embryos is obviously less than that of nature way, which indicates that the in vitro culture system for oocytes is not ideal. At the same time, the quality of the in vitro fertilized embryos also affects the pregnancy rate after embryo transplant, and the survival rate of offspring after transplant. Thus, optimizing and improving the system for in vitro maturation of oocytes will contribute to increase the number of oocytes that can be used for in vitro fertilization and producing an embryo, and promote the improvement of the embryo quality. Thus, perfecting the culture media and methods for culturing immature oocytes in vitro in the livestock embryo system to increase the in vitro maturation rate of oocytes will contribute to the improvement of efficiency of embryo engineering and reproduction of livestock.

In recent years, people have made several improvements to mammal oocyte in vitro maturation (IVM), and great developments have been made. The basic approach is: to developing a two-stage maturation culture method by simulating an in vivo environment of oocytes, i.e., by provisionally reversibly retarding the recovery of meiosis through using meiotic inhibitor in vitro, at the same time promoting the growth of oocytes and the maturation of cytoplasm; and then, the oocytes are removed from the meiotic inhibitory environment for in vitro maturation. The purpose of this method is: prolonging the time during which the granule cells and the oocytes exchange materials and information through the gap, and promoting the accumulation of mRNAs and proteins in oocytes.

For example, patent document CN102140435A discloses a culture medium for in vitro maturation of buffalo oocytes, which improves the maturation rate of buffalo oocytes through adding insulin, transferrin and selenium. CN101591637A discloses a culture medium for in vitro maturation of cattle oocytes, which improves the maturation rate of cattle oocytes through adding amniotic epithelial cells and the culture medium supernatant thereof to an IVM culture medium, using the character of amniotic epithelial cells, that is, the active materials secreted and synthesized by the amniotic epithelial cells. CN100432219C discloses a culture medium for in vitro maturation of cattle oocytes, which uses tea polyphenols as antioxidant having effects of anti-free radicals and stimulating intracellular antioxidant defense system, so as to obtain a culture medium that promotes in vitro maturation of cattle oocytes. CN102899286A discloses a culture medium for in vitro maturation of cattle oocytes, which improves the in vitro development ability through adding CNP to TCM199 culture medium, and CNP promotes synchronization of maturation of cell nucleus and cytoplasm.

The above methods either contribute to promoting the recovery of oocyte meiosis and in vitro mature; or achieve the goal of improving oocyte in vitro development ability through retarding unduly early oocyte meiosis.

SUMMARY

In order to solve the problems in the prior art, an object of the present disclosure is to provide a culture medium for in vitro maturation that increases the maturation rate and improves the development potential of the immature oocytes.

In order to achieve the goal of the present disclosure, the technical solution of the present disclosure is provided herein.

In one aspect, the present disclosure provides a culture medium for promoting in vitro maturation of immature oocytes, which comprises follicular granule cells and a culture solution for culturing the follicular granule cells, wherein the culture solution for culturing the follicular granule cells comprises CNP or variant or analogue thereof, and HDAC (histone deacetylase) inhibitor.

In one embodiment, the culture medium is obtained by culturing the follicular granule cells in the culture solution for 4~6 h.

In another embodiment, the HDAC inhibitor is selected from the group consisting of HDAC1 inhibitor, HDAC2 inhibitor and HDAC3 inhibitor.

Further, the HDAC inhibitor is HDAC3 inhibitor; and the HDAC3 inhibitor is selected from the group consisting of HDACi 4b, Entinostat (MS-275), BG45, RG2833 (RGFP109) and RGFP966, or a mixture thereof.

In another embodiment, CNP is C-type natriuretic peptide.

In another embodiment, the culture solution for culturing the follicular granule cells comprises 30~120 ng/mL of CNP or variant or analogue thereof, and 1~10 µM of HDAC inhibitor.

In a further embodiment, the culture solution for culturing the follicular granule cells comprises 40~80 ng/mL of CNP or variant or analogue thereof, and 3~7 µM of HDAC inhibitor.

In another embodiment, the culture solution for culturing the follicular cells further comprises: 5~15% of FBS, 0.01~0.5 mg/mL of glutamine, 10~200 IU/mL of penicillin and 10~200 IU/mL of streptomycin.

In a preferred embodiment, the culture solution for culturing the follicular cells is TCM199 medium containing 60 ng/mL of CNP or variant or analogue thereof, 5 µM of HDAC inhibitor, 10% FBS, 0.1 mg/mL of glutamine, 100 IU/mL of penicillin and 100 IU/mL of streptomycin.

In another aspect, the present disclosure further provides a culture solution for in vitro maturation, which is used for in vitro maturation of an immature oocyte, wherein the culture solution comprises CNP or variant or analogue thereof, and HDAC inhibitor, and through contacting with follicular granule cells, the culture solution further forms a culture medium for in vitro maturation of immature oocytes.

In one embodiment, the HDAC inhibitor is selected from the group consisting of HDAC1 inhibitor, HDAC2 inhibitor and HDAC3 inhibitor.

Further, the HDAC inhibitor is HDAC3 inhibitor; and the HDAC3 inhibitor is selected from the group consisting of HDACi 4b, Entinostat (MS-275), BG45, RG2833 (RGFP109) and RGFP966, or a mixture thereof.

In another embodiment, CNP is C-type natriuretic peptide.

In another embodiment, the culture solution comprises 30~120 ng/mL of CNP or variant or analogue thereof, and 1~10 µM of HDAC inhibitor.

In another embodiment, the culture medium comprises 40~80 ng/mL of CNP or variant or analogue thereof, and 3~7 µM of HDAC inhibitor.

In another embodiment, the culture medium further comprises one or more of: 5~15% of FBS, 0.01~0.5 mg/mL of glutamine, 10~200 IU/mL of penicillin and 10~200 IU/mL of streptomycin.

In a preferred embodiment, the culture medium further comprises one or more of: 5~10% FBS, 0.05~0.2 mg/mL of glutamine, 50~150 IU/mL of penicillin and 50~150 IU/mL of streptomycin. Preferably, the culture medium further comprises one or more of: 10% FBS, 0.1 mg/mL of glutamine, 100 IU/mL of penicillin and 100 IU/mL of streptomycin.

In a specific embodiment, the culture medium is TCM199 culture medium containing 60 ng/mL of CNP or variant or analogue thereof, 5 µM of HDAC inhibitor, 10% FBS, 0.1 mg/mL of glutamine, 100 IU/mL of penicillin and 100 IU/mL of streptomycin.

In another aspect, the present disclosure further provides a composition, which can be used for in vitro maturation of immature oocyte, consisting of CNP or variant or analogue thereof, and HDAC inhibitor; the composition is used for in vitro maturation of immature oocyte by being added to a common culture medium.

In one embodiment, when the composition is used for in vitro maturation culture of immature oocytes, it has a concentration in the culture medium of: 30~120 ng/mL of CNP or variant or analogue thereof, and 1~10 µM of HDAC inhibitor.

In another aspect, the present disclosure provides a culture method for promoting in vitro maturation of immature oocytes, comprising culturing the immature oocytes separated from a subject in the culture medium previously mentioned.

In a preferred embodiment, the method specifically is performed by: collecting granule cells from follicle of the object, performing a cell monolayer adherent culture in the culture solution for in vitro maturation to obtain feeder layer cells, collecting oocytes in the germinal vesicle stage, and culturing the oocytes in the culture solution containing the feeder layer cells for 20~25 h.

In one embodiment, the subject is human being, cattle, pig, sheep or rodents, and the like.

In another embodiment, the maturated oocytes can be used for parthenogenetic activation, in vitro fertilization or single sperm injection, thereafter subjected to embryo culture, and the embryos are used to embryo transplant for assisted reproduction or animal husbandry production.

In a preferred embodiment, when the subject is human being, the method specifically is performed by:
1) collecting granule cells and oocytes after digesting with hyaluronidase, respectively;
2) culturing the granule cells in the culture solution for in vitro maturation for adherent culture;
3) choosing the oocytes, which are still in the germinal vesicle-stage after digesting and culturing in vitro for 4~6 h, and placing the oocytes in the treated culture solution of step 2) for in vitro maturation containing feeder layer cells for culture.

In another aspect, the present disclosure further provides use of the previously mentioned culture solution for in vitro maturation for promoting in vitro maturation of immature oocytes.

Further, the present disclosure also provides use of the composition containing CNP or variant or analogue thereof and HDAC inhibitor in the manufacture of media for promoting meiosis recovery and development potential improvement of immature oocytes after superovulation in clinical.

The beneficial effects of the present disclosure are stated hereinafter.

For clinical human patients, in the present disclosure, oocytes that are not mature after treated with gonadotropin are subjected to maturation culture for the first time, this improves the maturation rate and post-stage development potential of the oocytes. The method not only makes full use of oocyte sources after superovulation, but also improves the development ability of early embryo after fertilization, increases the success rate of pregnancy of patients after assisted reproduction. For animals (e.g., mice), the culture of immature oocytes has the similar benefits.

In the method of the present disclosure, granule cells are used as feeder layer to induce the maturation of oocytes, and CNP or variant or analogue thereof and HDAC inhibitor are used to treat the granule cells derived from ovary follicle, by enhancing the expression and secretion of factors promoting oocyte development in granule cells, the in vitro development ability of oocytes is improved. Thus, this method may provide a new-type drug that promotes the maturation of oocytes, which may be widely used in clinic for human assisted reproduction.

CNP used in the present disclosure is a type of active peptide in follicle, which has low toxic effect on oocytes, and the toxic effect of HDAC inhibitor has been proved to be pretty weak on organism and oocyte.

BRIEF DESCRIPTION OF DRAWINGS

FIG. 1A shows that HDACi 4b promotes the maturation and development of human oocytes from germinal vesicle (GV) stage into metaphase II (MII) stage.

FIG. 1B shows that, in the control group and the treated group, the numbers of 2 pronucleus zygotes (2PN) obtained by performing ICSI fertilization on MII oocytes are basically the same.

FIG. 1C shows that the cleavage ability of HDACi 4b treated oocytes after fertilization is significantly improved.

FIG. 1D shows the blastocysts obtained from HDACi 4b induced mature oocytes after fertilization and the control group in vitro culture.

FIG. 1E shows the blastocyst counting results, indicating that the development ability of embryos obtained from HDACi4b induced mature oocytes is significantly increased.

FIG. 1F shows that inhibiting human ovary granule cells significantly promotes the expression of AREG.

FIG. 1G shows the immunofluorescence results of inner cell mass specific protein OCT4 and ectoderm specific protein CDX2, indicating that quality of blastocysts developed from HDACi 4b induced mature oocytes is significantly improved.

FIG. 2A shows that in an in vitro follicle culture model, HDACi 4b significantly promotes the recovery of oocyte meiosis in follicle of mouse.

FIG. 2B shows that in the culture medium for in vitro maturation, the ability for recovering meiosis of HDACi treated oocytes is similar to that of the control group.

FIG. 2C shows that HDACi 4b significantly promotes the oocyte to step over the first meiosis but retard at the metaphases II (MII).

FIG. 2D shows that the cleavage abilities after fertilization are basically the same in HDACi 4b induced mature oocytes group and the control group.

FIG. 2E shows that the ability to develop into an embryo from fertilized HDACi 4b induced mouse GV stage oocytes is significantly improved.

FIG. 2F shows that the ability to develop into a blastocyst from fertilized HDACi 4b treated oocytes is significantly increased.

FIG. 2G shows the blastocyst culture results of the control group and the HDACi 4b treated group.

FIG. 2H shows that blastocyst counting results, indicating that the ability to develop into a blastocyst from fertilized HDACi 4b treated GV stage oocytes is significantly increased.

FIG. 2I shows the immunofluorescence results of the inner cell mass specific protein OCT4, indicating that the quality of blastocysts from HDACi 4b treated oocytes is significantly increased.

DETAILED DESCRIPTION

Figure 1:
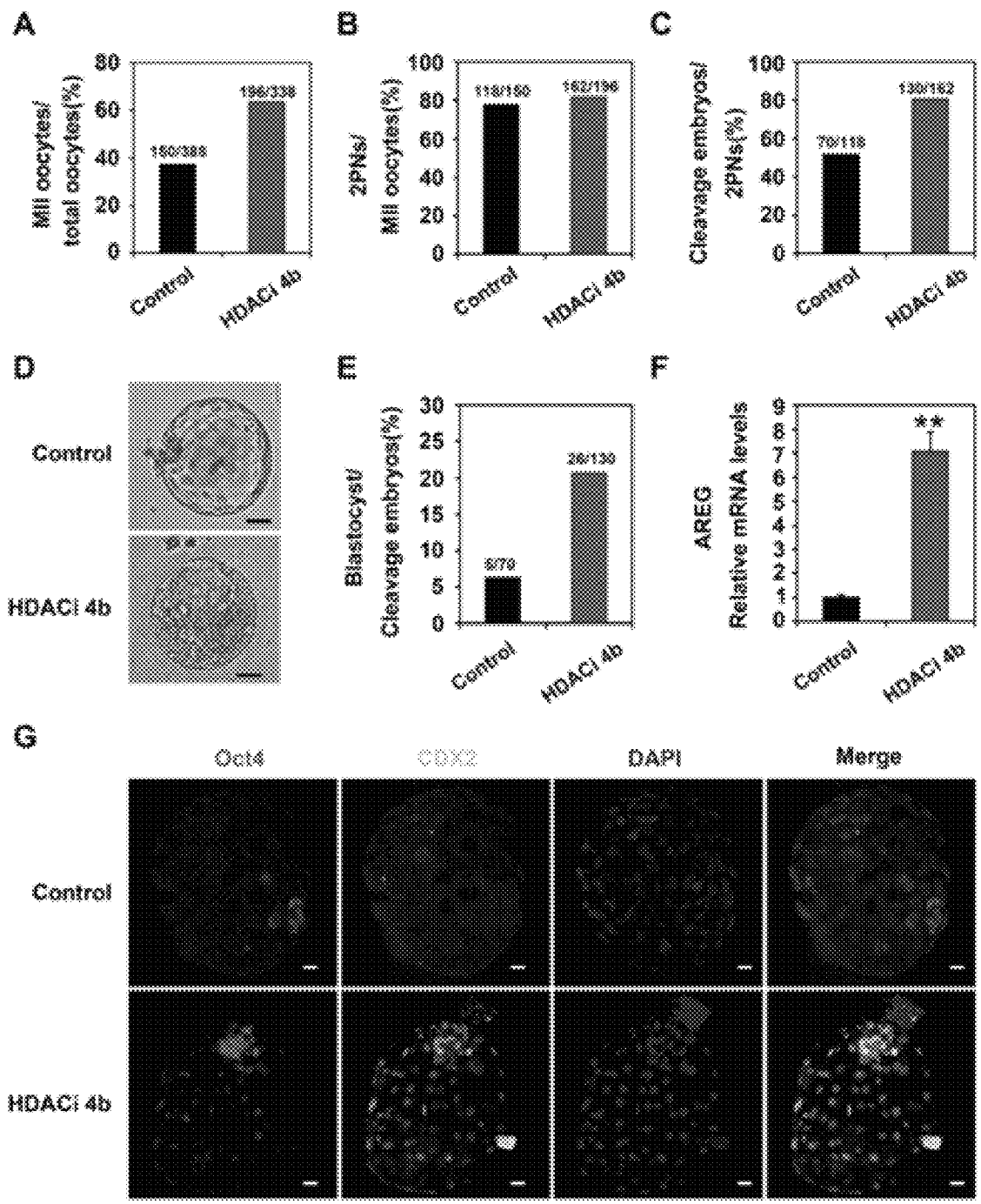
FIG. 1 shows effects of HDAC3 inhibitor HDACi 4b on promoting the maturation and development of human oocytes.

The present disclosure can be further understood through the following examples, wherein the examples show some methods for the preparation or use. However, it should be understood that these examples are not limitations to the present disclosure. The now known or further developed variations of the present disclosure are deemed to fall into the protection scope as described herein and as claimed below.

Definition of Terms

The meanings of terms used in the present specification are well-known to one of ordinary skill in the art. However, some of the terms are defined hereinafter for reference.

The term "culture medium" refers to a liquid environment for maintaining oocytes or embryos and for the proliferation of oocytes or embryos.

The term "separated" refers to collecting or purifying oocytes (at least part) from the natural environment. An example is, separated oocytes or denuded oocytes which are removed from an object as a part of follicle or cumulus oocyte complex.

The term "variant" refers to an amino acid sequence having one or more amino acid alterations. The variant may have a "conservative" alteration, in which the substituting amino acid has a similar structure or chemical characteristic as that of the substituted amino acid (e.g., replacing leucine with isoleucine). The variant may have one or more of "non-conservative" alteration (e.g., replacing glycine with tryptophan), or deletion and/or insertion.

The term "analogue" refers to a molecule that has a similar structure, regulation function or biochemical function comparing with the reference molecule, including biological active fragment of the reference molecule.

The term "subject" refers to a female mammal, including primates, livestock (e.g., horses, cattle, sheep, pigs and goats), companion animals (e.g., dogs and cats), laboratory test animals (e.g., mice, rats and guinea pigs), or meaningful animals in veterinary medicine.

The term "assisted reproduction" refers to any techniques that relate to producing a transplantable embryo, including oocytes or embryos in vitro culture (e.g., in vitro maturation of oocyte), in vitro fertilization (IVF: extracting oocytes, performing fertilization in a lab and transplanting the embryo to a receptor), gamete intrafallopian transfer (GIFT: setting oocytes and sperms in the fallopian tube), zygote intrafallopian transfer (ZIFT: setting the fertilized oocyte in the fallopian tube), tubal embryo transfer (TET: setting a divided embryo in the fallopian tube), intraperitoneal oocyte and sperm transplantation (POST: setting oocytes and sperms in the pelvic cavity), intracytoplasmic sperm injection (ICSI), testicular sperm extraction (TESE), microsurgical epididymal sperm extraction (MESA), nuclear transfer, totipotent stem cell expansion, and parthenogenetic activation, and other assisted reproduction methods known in the art.

A latest research shows that HL plays a key role in the improvement of development ability of oocytes through oocyte cytoplasm maturation induced by somatic cells (Chen J, Torcia S, Xie F, Lin C J, Cakmak H, Franciosi F, Horner K, Onodera C, Song J S, Cedars M I, Ramalho-Santos M, Conti M. Nat Cell Biol. 2013 Dec. 15 (12): 1415-23. doi: 10.1038/ncb2873. Epub 2013 Nov. 24).

Correspondingly, our experiments were performed by: under conditions of in vitro culture, simulating the effect of LH, which functions on granule cells to promote the maturation of oocytes in vivo, so as to achieve the goal of promoting the maturation of oocytes and meanwhile, improving the development potential. The results show that, in the presence of CNP, inhibiting the nuclear maturation of oocytes in a short period, and adding HDAC3 inhibitor to the culture medium having granule cells feeder layer, give a similar effect as that of LH, i.e., promoting granule cells to secrete EGF-like growth factors (e.g., AREG, EREG, etc.), therefore promoting the maturation of oocytes.

Our results show that, without using LH, but with the help the culture medium or culture solution of the present disclosure, the goal of promoting protein accumulation in oocyte cytoplasm, and promoting the maturation of oocytes in germinal vesicle stage, and increasing the development potential of oocytes in vitro.

The culture medium, culture solution and composition of the present disclosure can be individually packaged in suitable containers (normally sterile) in many ways of use or unit, e.g., in an ampoule or a bottle. These containers may be sealed after filling. For the purpose of stability and/or protein application, there may be other additives. The method for packaging each component may be the methods well-known in the art.

Culturing oocytes in the culture medium of the present disclosure not only improves the result of transplanting and assisted reproduction, but also decreases the failure of transplant, as well as miscarriage, including spontaneous abortion, pre-eclampsia, limited intrauterine growth, premature delivery and placental abruption; in addition, improving prognosis after birth through improving placenta development and/or reducing risks and/or possibilities of complications of pregnancy.

In one embodiment of the present disclosure, oocytes are human oocytes or oocytes of a mammal. Examples of applicable mammal comprise primates, livestock (e.g., horses, cattle, sheep, pigs and goats), companion animals (e.g., dogs and cats), and laboratory test animals (e.g., mice, rats and guinea pigs). In one embodiment, the oocyte is human oocyte.

The oocyte may be, e.g., a part of follicle, a part of cumulus oocyte complex (COC), or a bare oocyte.

The culture medium provided by the present disclosure is not only suitable for human oocytes, but also suitable for culturing oocytes and embryos from animals. Thus, the present disclosure can be not only used for assisted reproduction technology of human being, but also for animals, and other techniques for producing animal embryos, e.g., parthenogenetic activation, nuclear transfer and totipotent stem cell application.

Methods for collecting oocytes from suitable female donors and performing in vitro fertilization of oocytes in the art may be, e.g., in vitro fertilization of human described in *Textbook of Assisted Reproduction: Laboratory and Clinical Perspectives* (2003) (Editors Gardner, D. K., Weissman, A., Howies, C M" Shoham, Z. Martin Dunits Ltd, London, UK), and in vitro fertilization of cattle described in (2003) Laboratory Production of Cattle Embryos 2nd Edition, Gordon, I. CABI Publishing, Oxon, UK.

Variants of CNP are CNP molecule having one or more amino acid changes (comparing to wild-type) in the amino acid sequence. In one embodiment, the amino acid sequence of the variant shows a homology of larger than 75% comparing to wild-type CNP. In another embodiment, the amino acid sequence of the variant shows a homology of larger than 90% comparing to wild-type CNP. In another embodiment, the amino acid sequence of the variant shows a homology of larger than 95% comparing to wild-type CNP.

Analogues of CNP are molecules having a similar structure (i.e., structural analogue), regulation function (i.e., regulating analogue), or biochemical function (i.e., functional analogue) with CNP, including biological active fragments of CNP.

In the present disclosure, the concentration of CNP or variant or analogue thereof in the culture medium, culture solution or composition is 30~120 ng/mL. In some specific embodiments, the concentration of CNP or variant or analogue thereof in the culture medium, culture solution or composition is 30, 40, 50, 60, 70, 80, 90, 100, 110 or 120 ng/mL.

The concentration of HDAC inhibitor in the culture medium, culture solution or composition is 1~10 μM. In some specific embodiments, the concentration of HDAC inhibitor in the culture medium, culture solution or composition is 1, 2, 3, 4, 5, 6, 7, 8, 9 or 10 μM.

EXAMPLE 1 PREPARATION A CULTURE SOLUTION FOR IN VITRO MATURATION

FBS, HDACi 4b, CNP, glutamine, penicillin and streptomycin were dissolved in TCM-199 medium to prepare a TCM-199 medium containing 10% FBS, 5 μM HDACi 4b, 60 ng/mL CNP, 0.1 mg/mL glutamine, 100 IU/mL penicillin and 100 IU/mL streptomycin, i.e., the culture solution for in vitro maturation.

EXAMPLE 2 PREPARATION A CULTURE SOLUTION FOR IN VITRO MATURATION

FBS, HDACi 4b, CNP, glutamine, penicillin and streptomycin were dissolved in TCM-199 medium to prepare a TCM-199 medium containing 5% FBS, 3 μM HDACi 4b, 80 ng/mL CNP, 0.05 mg/mL glutamine, 100 IU/mL penicillin and 100 IU/mL streptomycin, i.e., the culture solution for in vitro maturation.

EXAMPLE 3 PREPARATION A CULTURE SOLUTION FOR IN VITRO MATURATION

FBS, HDACi 4b, CNP, glutamine, penicillin and streptomycin were dissolved in TCM-199 medium to prepare a TCM-199 medium containing 15% FBS, 7 μM HDACi 4b, 40 ng/mL CNP, 0.2 mg/mL glutamine, 100 IU/mL penicillin and 100 IU/mL streptomycin, i.e., the culture solution for in vitro maturation.

EXAMPLE 4 PREPARATION A CULTURE SOLUTION FOR IN VITRO MATURATION

HDACi 4b and CNP were dissolved in TCM-199 medium to prepare a TCM-199 medium containing 5 μM HDACi 4b and 60 ng/mL CNP, i.e., the culture solution for in vitro maturation.

EXAMPLE 5 PREPARATION A CULTURE SOLUTION FOR IN VITRO MATURATION

HDACi 4b and CNP were dissolved in TCM-199 medium to prepare a TCM-199 medium containing 1 μM HDACi 4b and 100 ng/mL CNP, i.e., the culture solution for in vitro maturation.

EXAMPLE 6 PREPARATION A CULTURE SOLUTION FOR IN VITRO MATURATION

HDACi 4b and CNP were dissolved in TCM-199 medium to prepare a TCM-199 medium containing 10 μM HDACi 4b and 30 ng/mL CNP, i.e., the culture solution for in vitro maturation.

EXAMPLE 7 PREPARATION A CULTURE SOLUTION FOR IN VITRO MATURATION

Granule cells and oocytes from different patients were provided by the assisted reproduction center of hospital and the donor sperms were provided by the sperm center.

Microdrop culture of granule cells: the cumulus oocyte complex collected from superovulation of patients were digested with hyaluronidase and then centrifuged to obtain the granule cells; the cells were cultured in the culture solution for in vitro maturation of examples 1~6 for microdroplet adherent culture respectively. The microdroplets were covered with liquid paraffin. After the granule cells adhered to the wall of the culture dishes, the resultants could be used as the culture medium 1~6 for in vitro maturation of immature oocytes.

EXAMPLE 8 IN VITRO MATURATION OF OOCYTES

The immature oocytes identified from superovulation of patients were put in the culture medium for in vitro maturation 1 (i.e., the culture medium obtained by using the culture solution for in vitro maturation of Example 1) containing feeder layer cells for microdrop culture. There were 1~2 oocytes per microdroplet, culture time 20~25 h, and culture conditions: 37° C., air with 5% $CO_2$ and 6% of $O_2$, and humidity 100%. The development results of the immature oocytes after microdroplet culturing in the culture medium for in vitro maturation 1 were shown in FIG. 1.

Intracytoplasmic sperm injection (ICSI) using the mature oocytes: the immature oocytes were culture in vitro for 20~25 h, the maturation status was observed. The oocytes reached the metaphase II (MII) were placed under micromanipulator for ICSI injection.

Embryo culture after fertilization: embryo culture medium G-1PLUS™ (Vitrolife, Sweden) was used to make several 50 μL microdroplets in a 35 mm culture dish. Mineral oil was covered on the surface of the droplets. This culture medium was suitable for culturing embryos from fertilized oocyte (0 day) to 8-cell embryo.

Embryo culture medium G-2 PLUS™ (Vitrolife. Sweden) was used to make several 50 μL microdroplets in a 35 mm Petri culture dish. Mineral oil was covered on the surface of the droplets. This culture medium was suitable for culturing embryos from 8-cell stage until blastocyst stage.

Comparing with the conventional method in the control group, the maturation rate of the human immature oocytes and the development rate of early embryos obtained by the method of the present disclosure were shown in Table 1. The experimental results showed that, after treating the oocytes with HDACi 4b+CNP for in vitro maturation for 20 h, the cleavage rate and blastocyst development rate of the treated oocytes after ICSI were significantly higher than that of the control group ($P<0.01$).

TABLE 1

Comparison of the results after culturing immature oocytes in different culture media

| Treatment (Number of Oocytes) | Cleavage Rate (%) | Blastocyst Development Rate (%) |
|---|---|---|
| Control group: culturing in a common medium for maturation for 24 h | 30.5 ± 2.8a | 8.3 ± 1.3c |
| Culture medium for in vitro maturation 1 for 20 h | 80.8 ± 2.4 b | 30.5 ± 4.3 d |

Comment: different letters in the same column indicates that the difference is significant ($P<0.01$); and cleavage rate=number of cleavage/number of oocytes, and blastocyst development rate=number of blastocysts/number of oocytes. The common medium for maturation was M199 culture medium.

Results: it could be concluded from the results above that adding composition HDACi 4b+CNP into the common culture medium significantly promoted the increase of maturation rate of immature oocytes, and the increase of the cleavage rate and blastocyst rate of the fertilized oocytes was 2~3 times of the control group.

In addition, it could be noted that the culture medium for in vitro maturation of examples 2~6 of the present disclosure (i.e., the culture mediums obtained by using the culture solution for in vitro maturation prepared in examples 2~6) also achieved a similar technical effect as that of Example 8, i.e., adding composition HDACi 4b+CNP to the common culture medium significantly promoted the increase of maturation rate of immature oocytes, and the increase of the cleavage rate and blastocyst rate of the fertilized oocytes was 2~3 times of the control group. Besides, similar effects were obtained after changing the type of HDAC3 inhibitor. The above results indicated that the culture medium and the method of the present disclosure were helpful for promoting the increase of maturation rate of immature oocytes and in vitro development ability. The method has potentially value in clinic and in animal husbandry.

EXAMPLE 9 IN VITRO MATURATION OF MOUSE IMMATURE OOCYTES

Figure 2:
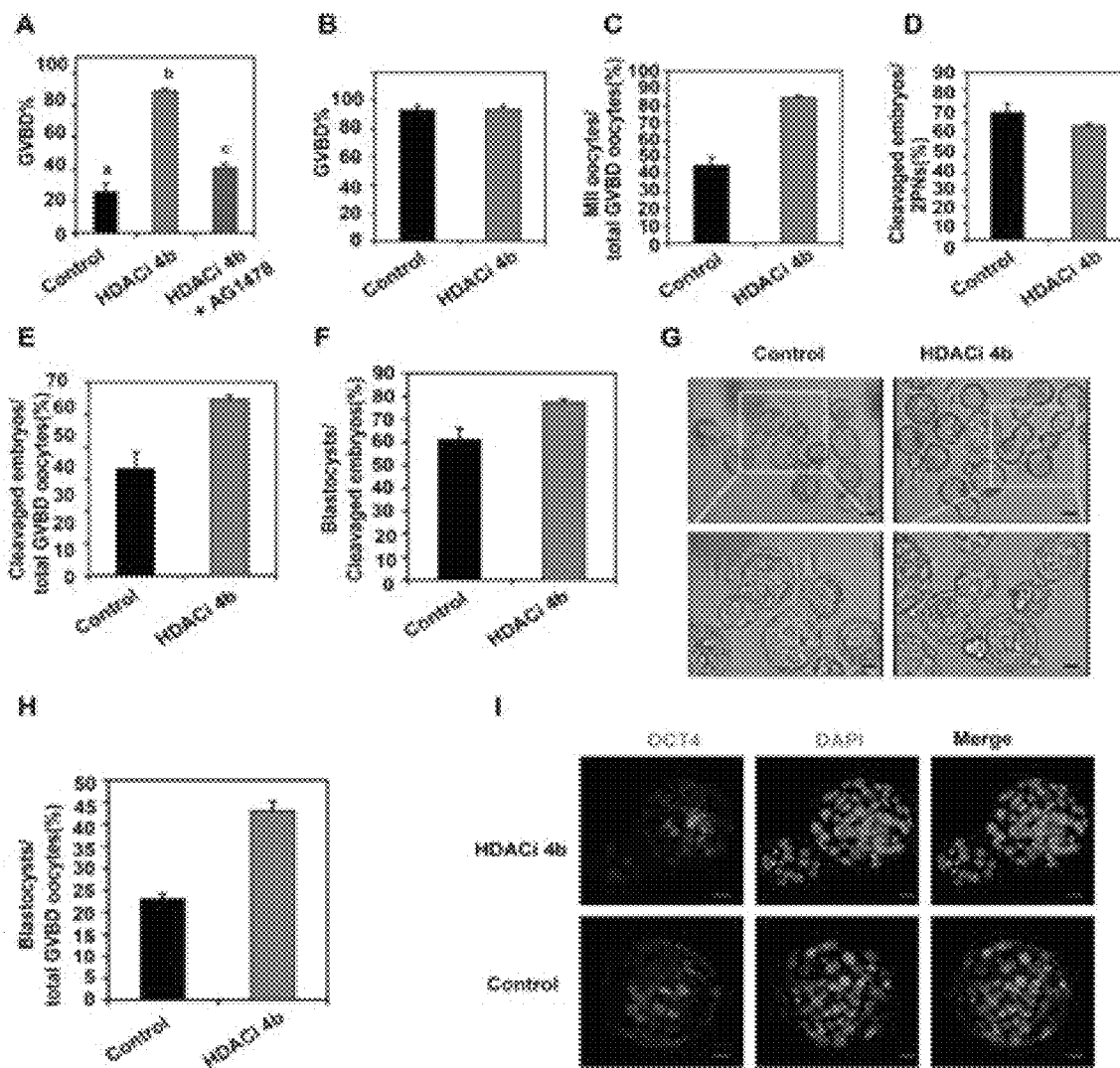
FIG. 2 shows that HDAC3 inhibitor HDACi 4b significantly promotes the maturation and development ability of mouse oocytes.

The specific culture method was referred to Example 8, and the differences were: instead of the granule cells form patients, granule cells from C57/BL6J mice were used; instead of the oocytes form patients, cumulus oocyte complexes form C57/BL6J mice were used. The results of in vitro development of the mouse oocytes were shown in FIG. 2.

Contents of the present disclosure merely illustrate some specific technical solutions that are claimed. Therein, the technical features described in one or more technical solutions may be combined with any one or more technical solutions, and the combined technical solutions are also within the protection scope of the present application, just as the combined technical solutions have been specifically described in contents of the present disclosure.

What is claimed is:

1. A culture medium, comprising follicular granule cells and a culture solution for culturing the follicular granule cells, wherein the culture solution for culturing the follicular granule cells comprises 30~120 ng/mL of C-type natriuretic peptide (CNP) and 1-10 μM of a histone deacetylase (HDAC) inhibitor, wherein the HDAC inhibitor is a HDAC3 inhibitor selected from the group consisting of HDACi 4b, Entinostat (MS-275), BG45, RG2833 (RGFP109) and RGFP966, or a mixture thereof.

2. The culture medium according to claim 1, wherein the culture medium is obtained by culturing the follicular granule cells in the culture solution for 4~6h.

3. The culture medium according to claim 1, wherein the culture solution for culturing the follicular granule cells comprises 40~80 ng/mL of CNP and 3~7 μM of a HDAC3 inhibitor.

4. The culture medium according to claim 1, wherein the culture solution for culturing the follicular granule cells further comprises: 5~15% of fetal bovine serum (FBS), 0.01~0.5 mg/mL of glutamine, 10~200 IU/mL of penicillin, and 10~200 IU/mL of streptomycin.

5. A culture solution for in vitro maturation of an immature oocyte, comprising 30-120 ng/mL of CNP and 1-10 μM of a HDAC inhibitor, and is conditioned through contacting the culture solution with follicular granule cells, wherein the HDAC inhibitor is a HDAC3 inhibitor selected from the group consisting of HDACi 4b, Entinostat (MS-275), BG45, RG2833 (RGFP109) and RGFP966, or a mixture thereof.

6. The culture solution for in vitro maturation according to claim 5, wherein the culture solution comprises 40~80 ng/mL of CNP, and 3~7 μM of HDAC inhibitor.

7. The culture solution for in vitro maturation according to claim 5, wherein the culture solution further comprises one or more of: 5~15% of FBS, 0.01~0.5 mg/mL of glutamine, 0~200 IU/mL of penicillin, and 10~200 IU/mL of streptomycin.

8. A method for promoting in vitro maturation of a immature oocyte, comprising a step of culturing the immature oocyte separated from a subject in the culture medium according to claim 1.

9. The method for promoting in vitro maturation of an immature oocytes according to claim 8, wherein the subject is a human, cattle, pig, sheep or rodent.

10. A The method of claim 8, wherein the subject undergoes superovulation in a clinic and wherein the method promotes the meiosis recovery and improves the development potential of immature oocytes after superovulation in the clinic.

11. A method for promoting the in vitro maturation of immature oocytes, comprising, collecting granule cells from a follicle of a subject, culturing the granule cells in a cell monolayer adherent culture in a culture solution comprising 30-120 ng/mL of CNP and 1-10 μM of a HDAC3 inhibitor to obtain feeder layer cells, collecting oocytes in the germinal vesicle stage from the subject, and culturing the oocytes in the culture solution containing the feeder layer cells for 20~25h, wherein the HDAC inhibitor is a HDAC3 inhibitor selected from the group consisting of HDACi 4b, Entinostat (MS-275), BG45, RG2833 (RGFP109) and RGFP966, or a mixture thereof.

12. The method for promoting the in vitro maturation of immature oocytes according to claim 11, wherein the subject is a human, and the method further comprises:
   a) collecting the granule cells and oocytes after digesting with hyaluronidase;
   b) selecting an oocyte, which is still in the germinal vesicle-stage after digesting and
   c) culturing the selected oocyte in vitro for 4-6h prior to culturing the oocyte in the culture solution containing the feeder layer cells.

* * * * *